(12) United States Patent
Beaulieu

(10) Patent No.: US 8,109,869 B2
(45) Date of Patent: Feb. 7, 2012

(54) VIBRATOR

(76) Inventor: Natasha Yee Beaulieu, Surrey (CA)

( * ) Notice: Subject to any disclaimer, the term of this patent is extended or adjusted under 35 U.S.C. 154(b) by 452 days.

(21) Appl. No.: 12/453,450

(22) Filed: May 12, 2009

(65) Prior Publication Data

US 2010/0292531 A1 Nov. 18, 2010

(51) Int. Cl.
*A61F 5/00* (2006.01)

(52) U.S. Cl. .......................................... 600/38; 601/46

(58) Field of Classification Search .............. 600/38–41; 601/46, 71
See application file for complete search history.

(56) References Cited

U.S. PATENT DOCUMENTS

| | | | |
|---|---|---|---|
| 3,626,931 A | 12/1971 | Bysakh | |
| 3,710,784 A | 1/1973 | Taylor | |
| 3,896,795 A | 7/1975 | Solhkhah | |
| 4,055,169 A | 10/1977 | Baker et al. | |
| 4,697,580 A | 10/1987 | Terauchi | |
| 4,732,140 A | 3/1988 | Stoffregen | |
| 5,334,131 A | 8/1994 | Omandam et al. | |
| 6,179,775 B1 | 1/2001 | Thompson | |
| 6,547,717 B1 | 4/2003 | Green et al. | |
| 6,579,229 B1 | 6/2003 | Nan | |
| 6,991,598 B2 | 1/2006 | Klein | |
| 6,991,600 B1 * | 1/2006 | Wang | 600/38 |
| 2002/0029008 A1 | 3/2002 | Pow Wong et al. | |
| 2004/0186343 A1 * | 9/2004 | Moore-Steele | 600/38 |
| 2006/0030749 A1 | 2/2006 | Hung et al. | |
| 2006/0142638 A1 | 6/2006 | Flores | |
| 2007/0038019 A1 * | 2/2007 | Weng | 600/38 |
| 2008/0306331 A1 * | 12/2008 | Morreale et al. | 600/38 |

FOREIGN PATENT DOCUMENTS

WO  WO 01/35895 A1  5/2001

* cited by examiner

*Primary Examiner* — John Lacyk

(57) ABSTRACT

Disclosed is an apparatus to be worn by a user for providing sexual stimulus to a partner of the user. The apparatus comprises a harness to be worn by the user and a vibrating body supported by the harness. The vibrating body has at least one protrusion extending therefrom. The apparatus further comprises a pad securable to the vibrating body. The pad has at least one void corresponding to the at least one protrusion. The at least one void surrounds the at least one protrusion when the pad is secured to the vibrating body. The pad also has a bearing surface for transmitting vibrations from the vibrating body and the at least one protrusion to a surface of the user's partner's body.

17 Claims, 7 Drawing Sheets

VIBRATOR

BACKGROUND OF THE INVENTION

1. Field of Invention

The present invention relates to sexual devices in general and in particular to an apparatus for providing vibratory stimulus to the partner of the user.

2. Description of Related Art

Sexual climax or orgasm is frequently a desired result of sexual activity. However, many women have difficulty achieving sexual climax or orgasm without direct clitoral stimulation. Thus during sexual intercourse in which no direct clitoral stimulation occurs many women are not able to have an orgasm. For such women, other methods are necessary to achieve orgasm, such as, oral sex or manual or vibratory stimulation. Use of these methods is not currently possible during face to face positions.

Additional difficulties exist within female same-sex couples related to difficulty achieving orgasm. For such couples, many sexual positions do not achieve sufficient clitoral stimulation to achieve orgasm. For example, during face to face positions between female same-sex couples is often difficult for many women to have an orgasm.

Previous sexual aids have not adequately addressed the above difficulty. For example, devices to be worn by a male during intercourse, such as, for example U.S. Patent Application Publication No. US2006/0030749 to Hung et al. are intended to be worn around the penis of a male user and are not therefore adapted to be worn by a female for female same-sex couples. Other devices, such as, for example, U.S. Pat. No. 6,547,717 to Green et al. are intended to be worn by female users only and do not directly stimulate the clitoris of the user's partner. Furthermore, other devices, such as, U.S. Pat. No. 6,991,598 to Klein stimulate the clitoris of the user instead of her partner. None of the previous devices enables a user to directly stimulate the clitoris of his or her partner during sexual activities to help her achieve orgasm.

SUMMARY OF THE INVENTION

According to a first embodiment of the present invention there is disclosed an apparatus to be worn by a user for providing sexual stimulus to a partner of the user. The apparatus comprises a harness to be worn by the user and a vibrating body supported by the harness. The vibrating body has at least one protrusion extending therefrom. The apparatus further comprises a pad securable to the vibrating body. The pad has at least one void corresponding to the at least one protrusion. The at least one void surrounds the at least one protrusion when the pad is secured to the vibrating body. The pad also has a bearing surface for transmitting vibrations from the vibrating body and the at least one protrusion to a surface of the user's partner's body.

The vibrating body may include a plurality of protrusions wherein the pad includes a plurality of voids for surrounding the plurality of protrusions. The plurality of protrusions may correspond to the plurality of voids. The plurality of protrusions and the plurality of voids may be arranged in a regular array.

The vibrating body may include a vibration drive motor. The vibration drive motor may be a variable speed motor. The apparatus may further comprising a drive motor control for controlling the speed of the variable speed motor. The drive motor control may be located on the harness.

The harness may further include a mounting plate. The vibrating body may be secured to the mounting plate wherein the pad is secured to the vibrating body. The pad may be formed from a material selected from the group consisting of silicone, rubber, elastomers, foams and latex. The mounting plate may include an arcuately shaped lower edge adapted to be located adjacent to the genitals of a male wearer. The pad may further include an arcuately shaped lower edge corresponding to the arcuately shaped lower edge of the mounting plate and being adapted to be located adjacent to the genitals of a male wearer.

The protrusions may have distal ends wherein the bearing surface of the pad includes raised portions corresponding to the distal ends of the protrusions. The cavities may comprise bores extending through the pad wherein the at least one protrusion extends through the bores. The pad may include side walls extending therefrom for surrounding the vibrating body. The harness may be adapted to locate the vibrating motor and the pad proximate to a pelvic region of the user.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
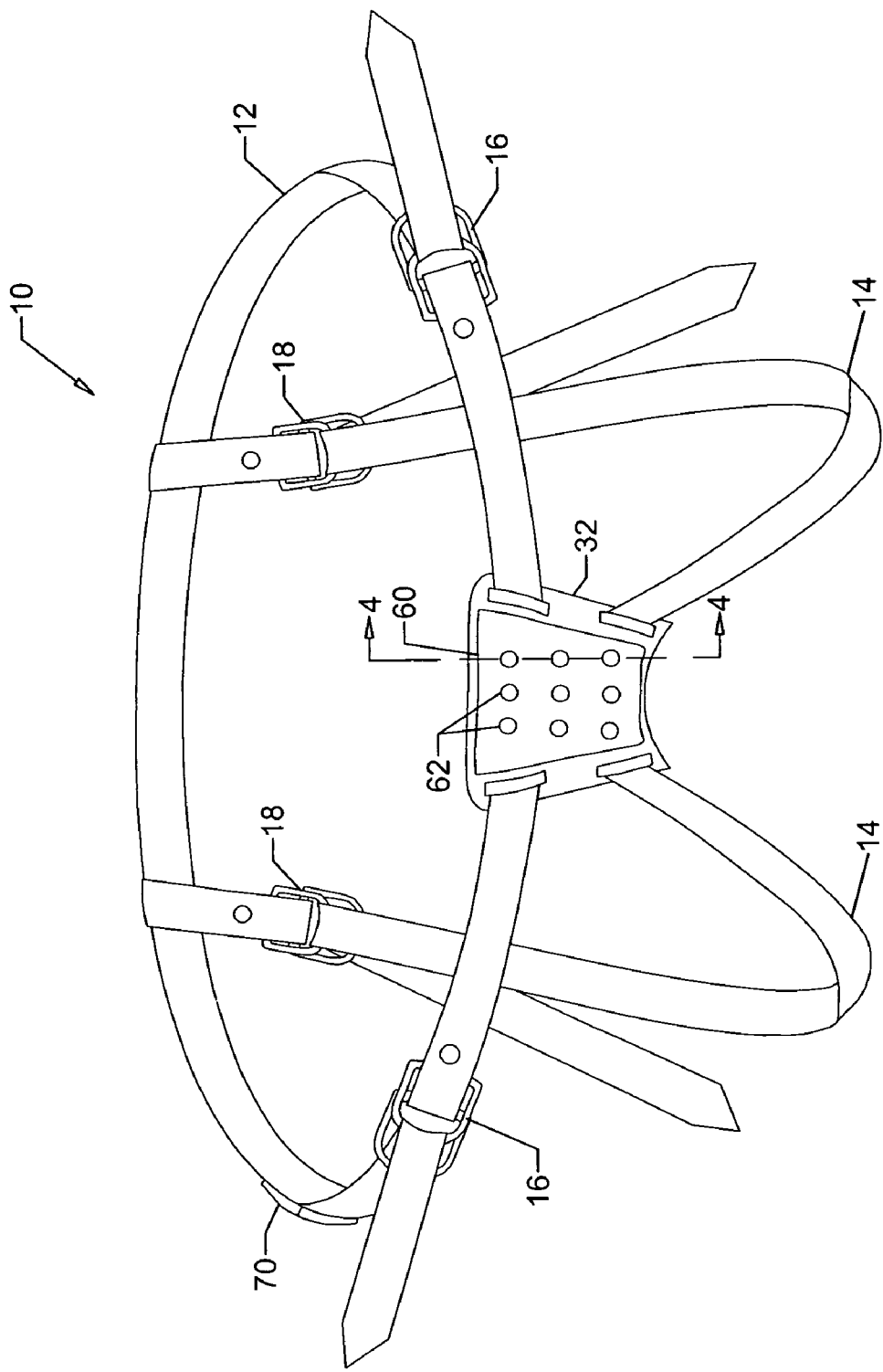
FIG. 1 is a perspective view of an apparatus according to a first embodiment of the present invention.

Referring to FIG. 1, an apparatus according to a first embodiment of the invention is shown generally at 10. The apparatus 10 comprises a vibrating body 20, a waist strap 12 and two thigh straps 14. The vibrating body 20 includes a plurality of protrusions 22 extending therefrom. The apparatus 10 further includes a control interface 70 for controlling the vibration speed of the vibrating body 20 as will be further described below.

Figure 2:
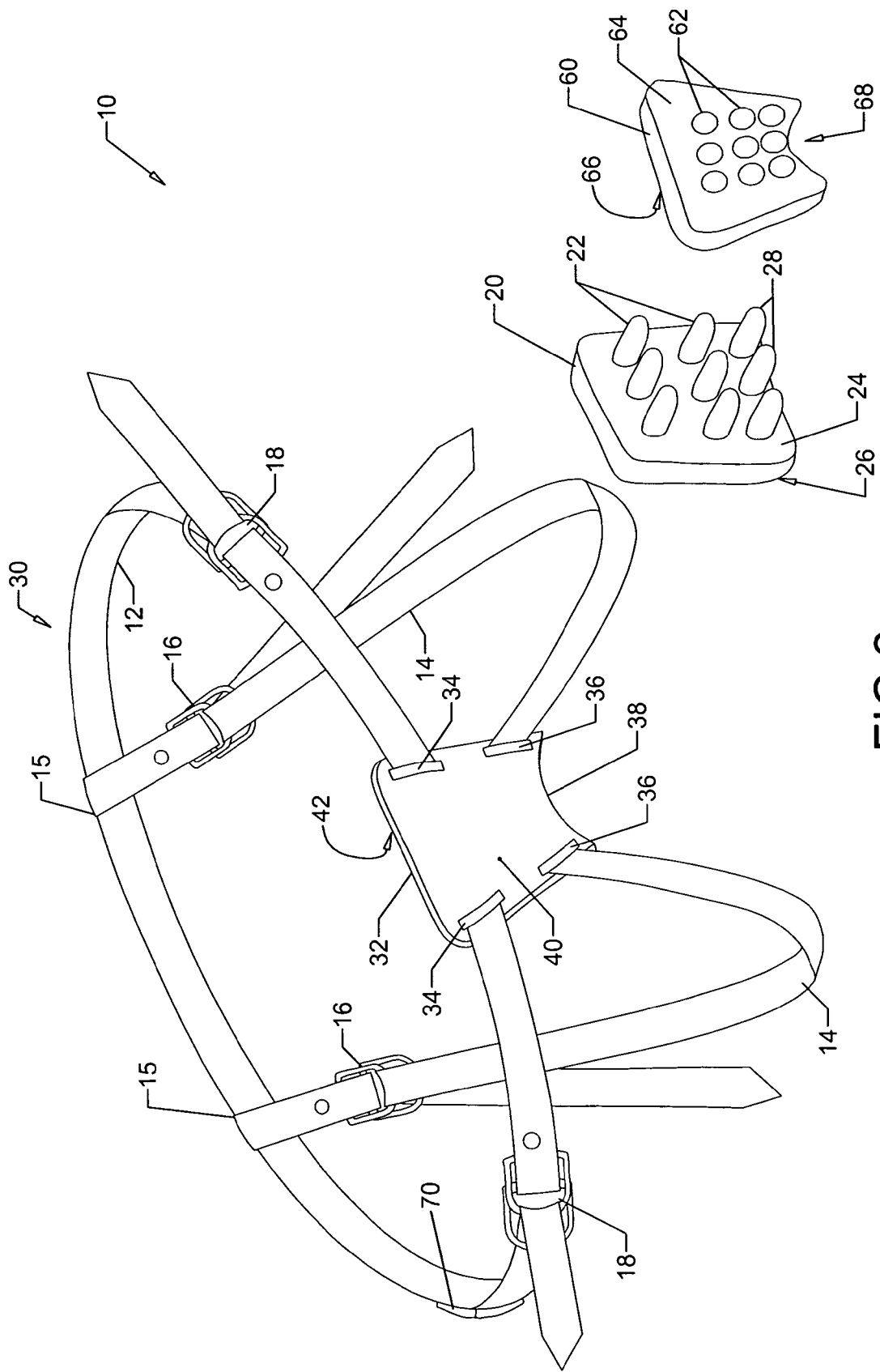
FIG. 2 is an exploded view of the apparatus of FIG. 1.
Figure 3:
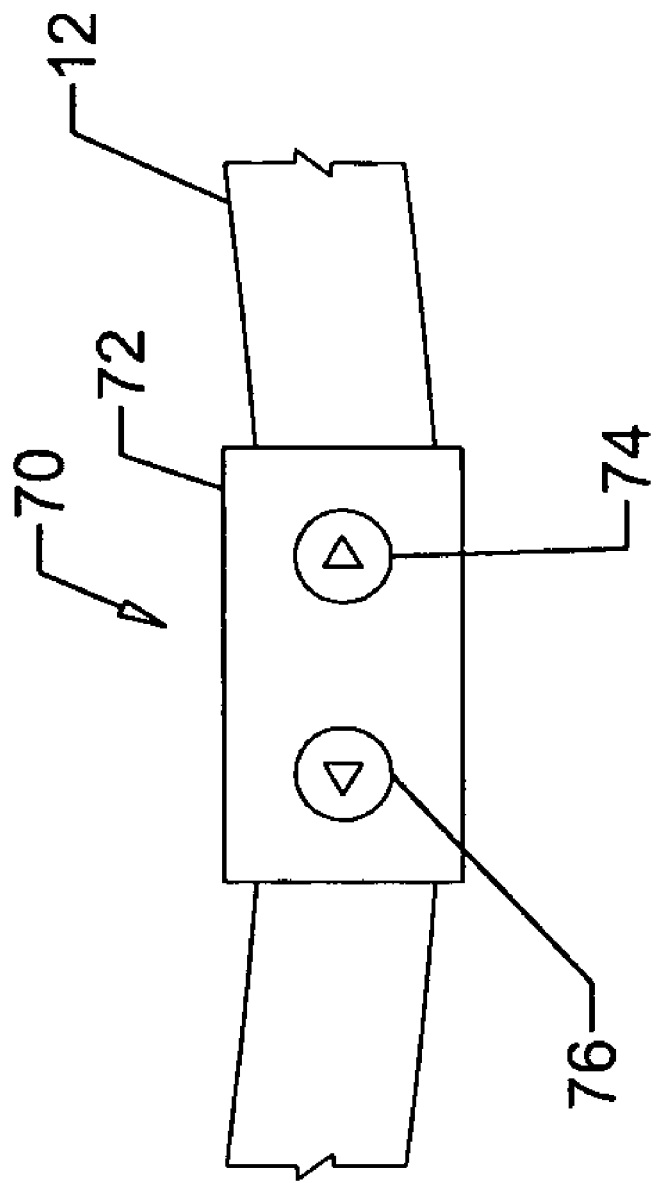
FIG. 3 is a front view of the control panel of the apparatus of FIG. 1.

Turning now to FIG. 2, an exploded view of the apparatus 10 is illustrated. The apparatus includes a harness 30, a vibrating body 20 and a pad 60. The harness includes the waist strap 12, two thigh straps 14 and a mounting plate 32. As illustrated, the thigh straps may be secured at their distal ends 15 to the waist strap 12. The waist strap 12 and thigh straps 14 may also include adjusting buckles 16 and 18, respectively for adjusting the fit of the harness. The adjusting buckles 16 and 18 may be of any known type, such as for example a belt buckle engaging within belt holes, D-ring type buckles, friction buckles, or mating buckles by way of non-limiting example. It will also be appreciated that although a waist belt harness with two thigh straps are illustrated and described, other harness types may also be useful for locating the vibrating body 20 at the appropriate position as desired by a user as further described below.

The mounting plate 32 comprises a substantially flat body having a front surface 40 and rear surface 42. The mounting plate 32 includes two waist slots 34 and two thigh slots 36 for securing the waist strap 12 and the thigh straps 14 thereto, respectively. As illustrated, the mounting plate 32 may also include a lower edge 38 having an arcuate shape.

The vibrating body 20 comprises a body having front and rear surfaces 24 and 26, respectively. Located within the vibrating body 20 is a vibrating motor (not shown) as is conventionally known in the art. The vibrating motor may comprise a rotating electrical motor with an eccentrically weighted shaft. The body of the vibratory body 20 may be constructed of any suitable material such as plastic, rubbers or the like. The vibratory body 20 may be secured to the mounting plate 32 by any known method such as, screws, clips, adhesives or latches by way of non-limiting example.

The protrusions 22 extend from the front surface 24. As illustrated the protrusions may extend normally from the front surface, although it will be appreciated that the protrusions may extend from the front surface at other angles as well. Additionally, the protrusions 22 may also extend from the front surface 24 parallel to each other although other relative orientations to each other may also be useful. In the embodiment illustrated, the apparatus 10 includes 9 protrusion arranged in a regular 3 by 3 array although other numbers and arrangements of protrusions may also be utilized. The protrusions 22 extend from the front surface 24 at a distance of between ¼ and 1 inch. In particular it has been found that protrusion lengths of between ¼ and ½ inch have been particularly useful. The protrusions may be formed of the same material as the vibratory body 20 or may optionally be formed of a different material and adhered thereto. In such embodiments, the protrusions 22 may be formed of any suitable material to transmit vibration therethrough, such as, by way of non-limiting example, vinyl, acrylic, latex, plastic or rubber coated metal or elastomers. The protrusions 22 may be secured to the vibratory body 20 by any known method, such as, for example, by threaded lugs, screwing, using adhesives or unit casting with the vibratory body. The protrusions 22 may have a circular or any other suitable cross section and may be substantially cylindrical or may have a taper from the front surface 24 of the vibrating body 20 to their distal ends 28. The distal ends 28 of the protrusions may have a domed, tapered, or pointed shape as desired by the user.

Figure 4:
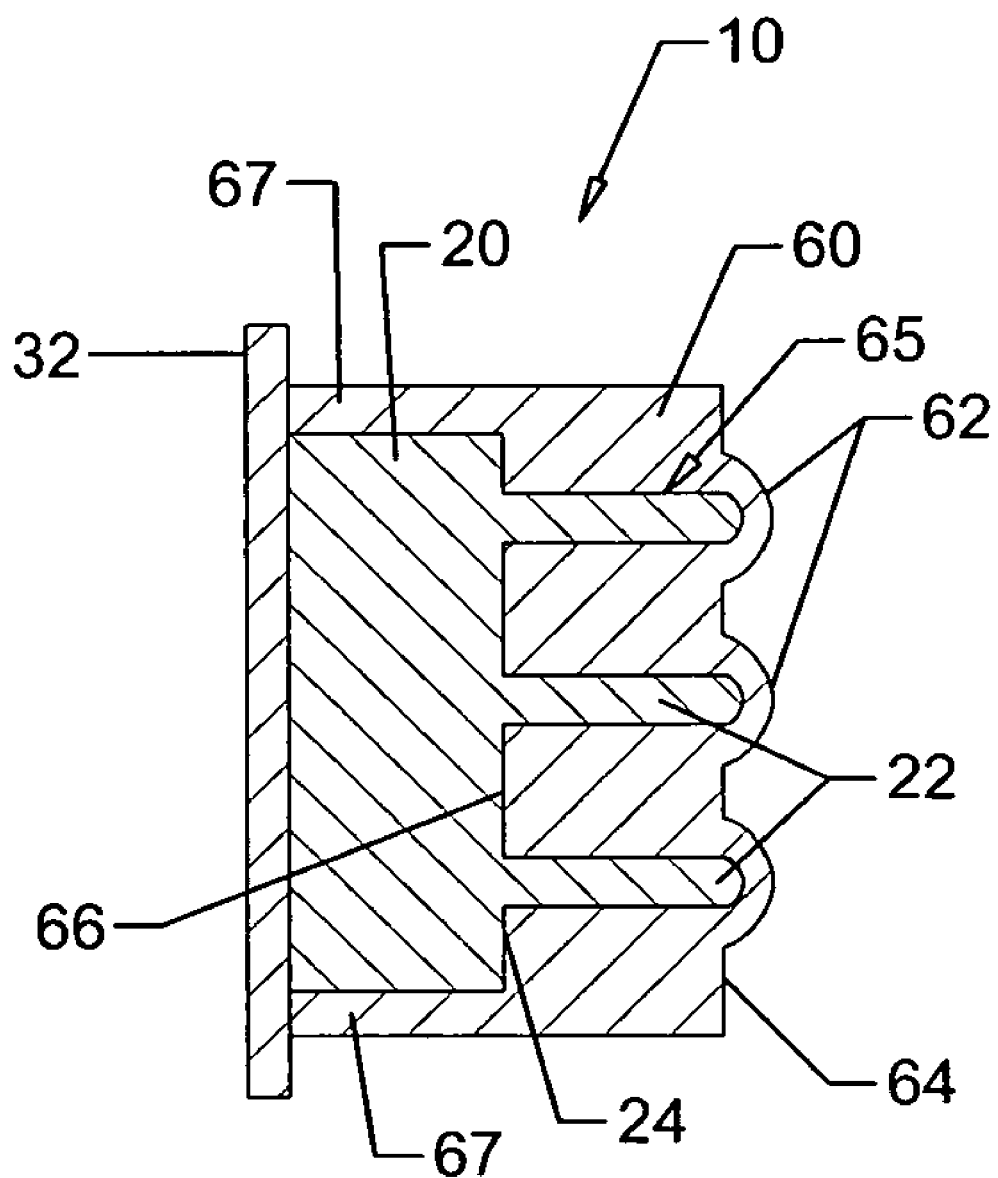
FIG. 4 is a cross-sectional view of the apparatus of FIG. 1 taken along the line 4-4 according to a first embodiment of the present invention having enclosed protrusions.
Figure 5:
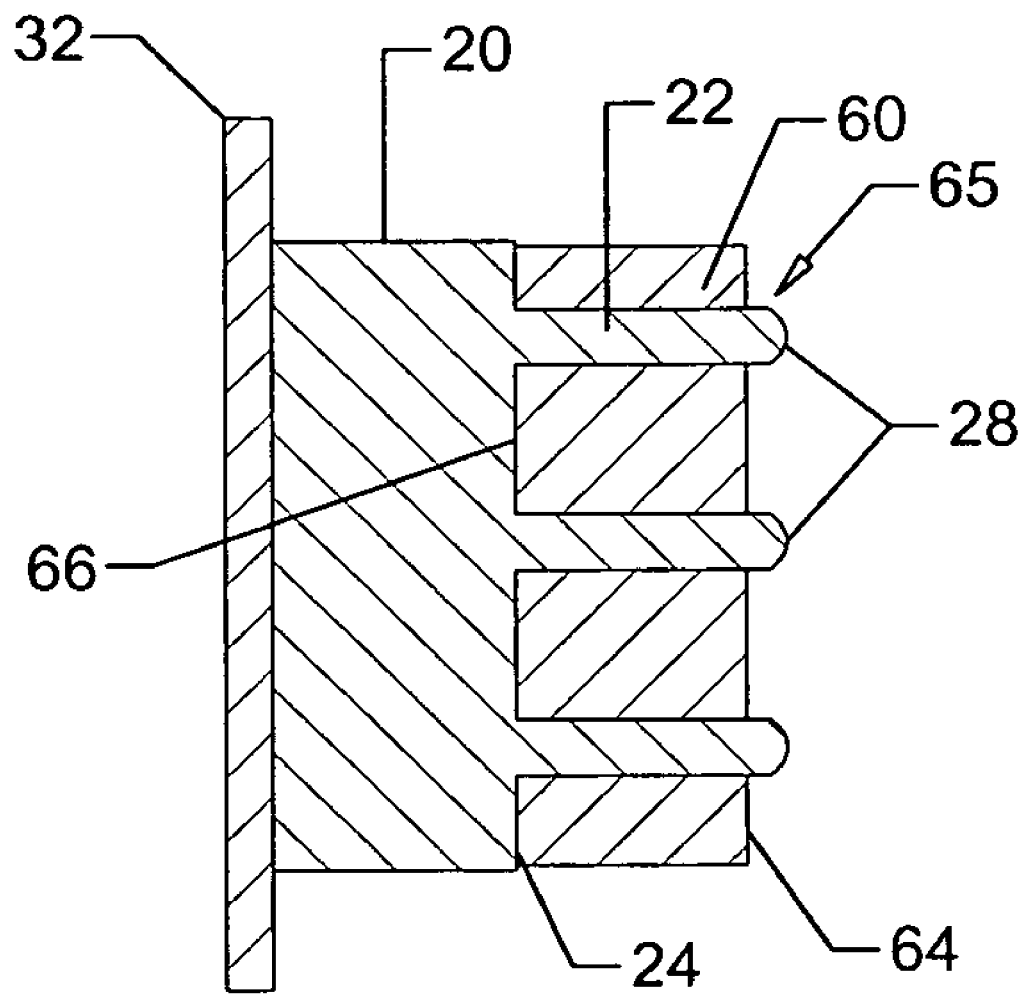
FIG. 5 is a cross-sectional view of the apparatus of FIG. 1 taken along the line 4-4 according to a further embodiment of the present invention having exposed protrusions.
Figure 6:
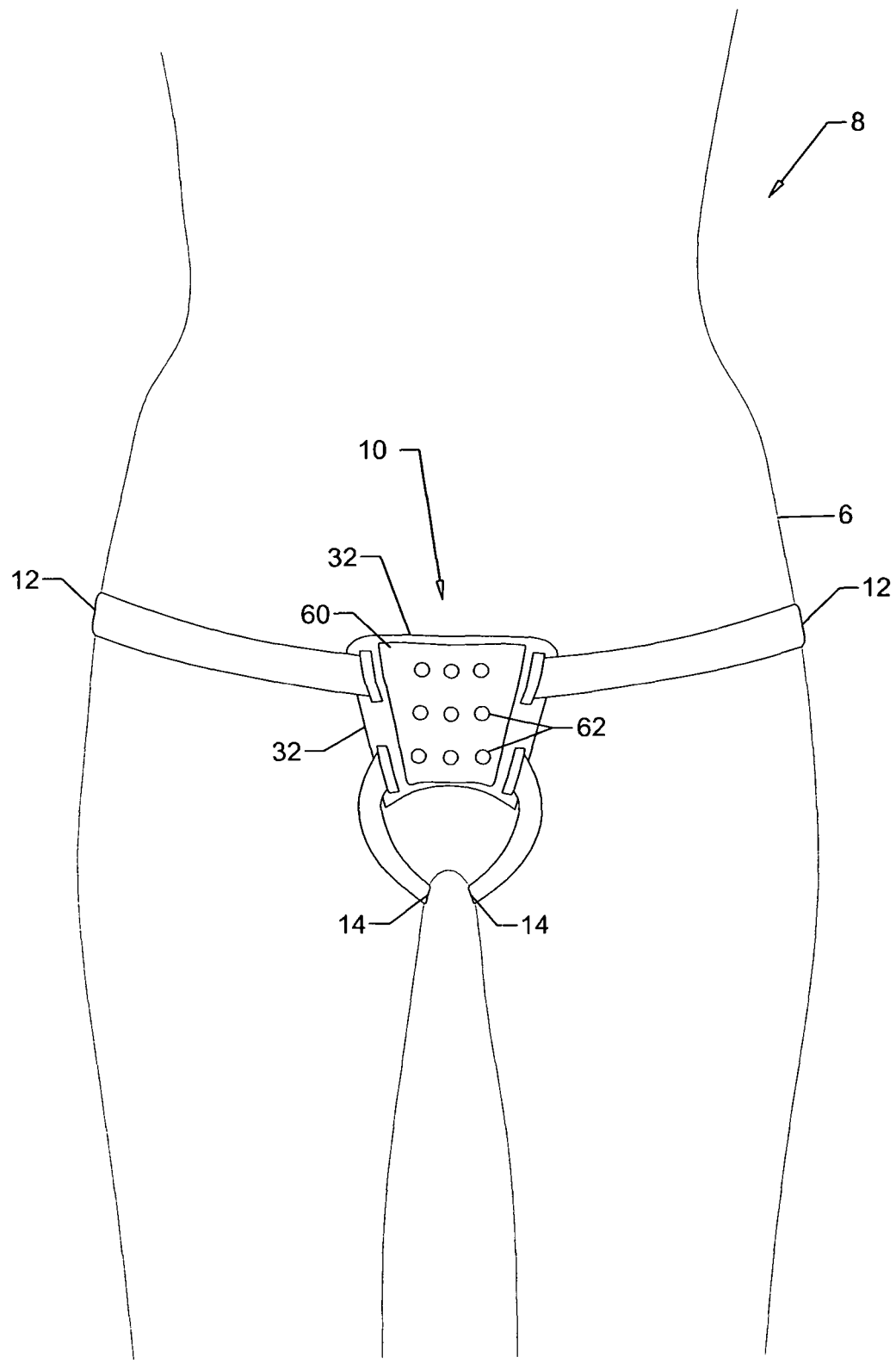
FIG. 6 is a front view of a female user wearing the apparatus of FIG. 1
Figure 7:
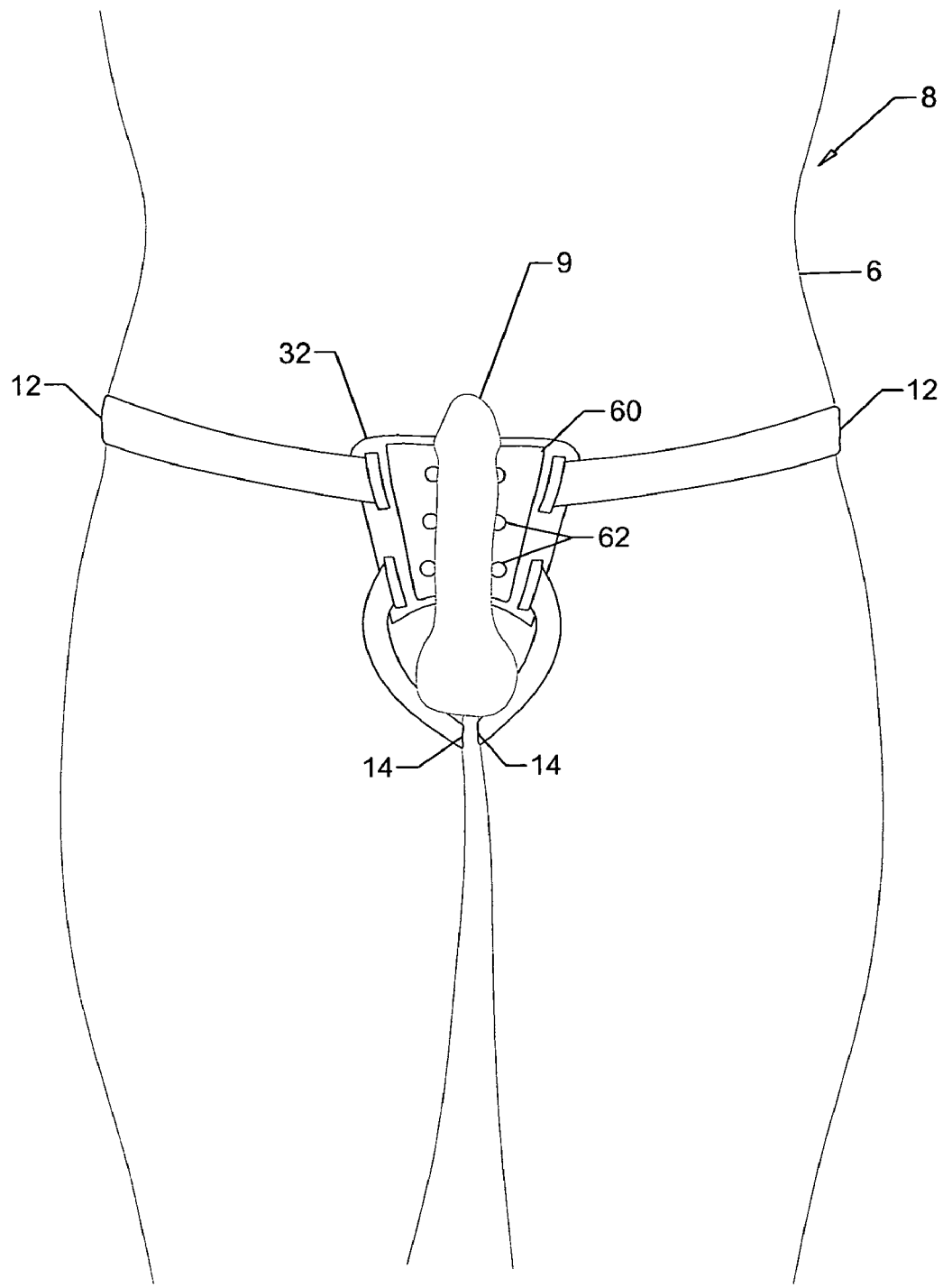
FIG. 7 is a front view of a male user wearing the apparatus of FIG. 1.

The pad 60 comprises a body of semi-rigid material for providing cushioning between the vibratory body 20 and the partner of the user. The pad 60 may be formed of any know material suitable for cushioning and for use in a sexual device, such as, for example, silicone, rubber, elastomers, foams or latex. The pad 60 has a rear surface 66 and a bearing or front surface 64 with a plurality of raised portions 62 extending therefrom. The pad 60 may also include a bottom edge 68 having an arcuate shape. The raised portions 62 have cavities 65 therebehind for receiving the protrusions 22 of the vibrating body 20 therein when the rear surface 66 of the pad 60 is secured to the front surface 24 of the vibrating body 20 as illustrated in FIG. 4. The cavities 65 behind the raised portions 62 may be sized to closely surround the protrusions 22. The pad 60 has a thickness sufficient to permit the raised portions 62 to cover the distal ends 28 of the protrusions 22. The pad 60 may optionally have a side wall 67 adapted to surround the vibrating body 20 when the pad is secured thereto as illustrated in FIG. 4. In an alternative embodiment as illustrated in FIG. 5, the pad 60 may omit one or both of the side walls 67 or the raised portions 22. In such an embodiment the cavities 65 comprise bores that permit the protrusions 22 to pass therethrough so as to extend past the front surface 64 of the pad 60. The pad 60 may be secured to the vibrating body 20 by any know means, such as, by way of non-limiting example, gluing, screwing, or friction fit.

Turning now to FIG. 2, the control interface 70 is illustrated. The control interface 70 comprises a control interface body 72 having a speed increase button 74 and a speed decrease button 76. The control interface body 72 is secured to the waist strap 12 or to any other desired location on the harness. Control wires (not shown) are run through or along the harness to the vibrating motor in the vibrating body 20 to control the speed or intensity of the vibrations created thereby. The speed increase button 74 will increase the speed of the vibration motor and therefore the frequency while the speed decrease button will decrease the speed of the vibration motor and therefore the frequency of the vibrations thus created.

In operation, the harness 30 is worn by a user as illustrated in either FIG. 4 or 5 with the vibrating body 20 secured to the mounting plate 32 and the pad 60 secured to the vibrating body. The may be applied to the body of the user such that the vibrating body 20 is located proximate to the pelvic region of the user. Thereafter, the user may engage in sexual activities with their partner such that the protrusions 22 or the raised portions 62 of the front surface 64 and the vibration of the vibrating body 20 stimulate the clitoris of the partner so as to assist the user's partner in achieving orgasm. It will be appreciated that the user and their partner may use the apparatus of the present invention in a variety of positions.

Turning now to FIG. 4, the apparatus 10 is shown applied to the body 6 of a female user 8. In particular, a user may chose the wear the apparatus 10 applied to their mons or pubic region for use in grinding against their partner. The vibrating body 20 of the apparatus 10 may be secured to the body 6 by a waist strap 12 and two thigh straps 14. As illustrated in FIG. 5, the apparatus 10 may also be applied to the body 6 of a male user 8. As illustrated, the vibrating body 20 may be secured to the body 6 in a similar manner such that the lower edges 38 and 68 of the mounting plate 32 and pad 60 are proximate to the top of the genitals 9 of the male wearer 8. It will therefore be appreciated that when an apparatus according to one embodiment of the present invention is thus worn by a male user, he will be able to stimulate the clitoris of his female partner during face to face, or missionary position sexual intercourse.

While specific embodiments of the invention have been described and illustrated, such embodiments should be considered illustrative of the invention only and not as limiting the invention as construed in accordance with the accompanying claims.

What is claimed is:

1. An apparatus to be worn by a user for providing sexual stimulus to a partner of the user, the apparatus comprising:
   a harness to be worn by the user;
   a vibrating body supported by said harness, said vibrating body having at least one protrusion extending therefrom; and
   a pad securable to said vibrating body having at least one void corresponding to said at least one protrusion, wherein said at least one void surrounds said at least one protrusion when said pad is secured to said vibrating body, said pad having a bearing surface for transmitting vibrations from said vibrating body and said at least one protrusion to a surface of the user's partner's body.

2. The apparatus of claim 1 wherein said vibrating body includes a plurality of protrusions, wherein said pad includes a plurality of voids for surrounding said plurality of protrusions.

3. The apparatus of claim 2 wherein said plurality of protrusions correspond to said plurality of voids.

4. The apparatus of claim 3 wherein said plurality of protrusions and said plurality of voids are arranged in a regular array.

5. The apparatus of claim 1 wherein said vibrating body includes a vibration drive motor.

6. The apparatus of claim 5 wherein said vibration drive motor is a variable speed motor.

7. The apparatus of claim 6 further comprising a drive motor control for controlling the speed of said variable speed motor.

8. The apparatus of claim 1 wherein said harness further includes a mounting plate.

9. The apparatus of claim 8 wherein said drive motor control is located on said harness.

10. The apparatus of claim 8 wherein said vibrating body is secured to said mounting plate, wherein said pad is secured to said vibrating body.

11. The apparatus of claim 10 wherein said pad is formed from a material selected from the group consisting of silicone, rubber, elastomers, foams and latex.

12. The apparatus of claim 10 wherein said mounting plate includes an arcuately shaped lower edge adapted to be located adjacent to the genitals of a male wearer.

13. The apparatus of claim 12 wherein said pad further includes an arcuately shaped lower edge corresponding to said arcuately shaped lower edge of said mounting plate and being adapted to be located adjacent to the genitals of a male wearer.

14. The apparatus of claim 1 wherein said protrusions have distal ends, wherein said bearing surface of said pad includes raised portions corresponding to said distal ends of said protrusions.

15. The apparatus of claim 1 wherein said cavities comprise bores extending through said pad wherein said at least one protrusion extends through said bores.

16. The apparatus of claim 1 wherein said pad includes side walls extending therefrom for surrounding said vibrating body.

17. The apparatus of claim 1 wherein said harness is adapted to locate said vibrating motor and said pad proximate to a pelvic region of the user.

\* \* \* \* \*